United States Patent [19]

Mehmanesh et al.

[11] Patent Number: 5,527,358

[45] Date of Patent: Jun. 18, 1996

[54] TEMPORARY MEDICAL ELECTRICAL LEAD

[75] Inventors: Hormoz Mehmanesh; Werner Saggau, both of Heidelberg, Germany; Karel F. A. A. Smits, Oirsbeck; Chrit W. Dreessen, Stein, both of Netherlands

[73] Assignee: Medtronic, Inc., Minneapolis, Minn.

[21] Appl. No.: 184,712

[22] Filed: Jan. 21, 1994

[51] Int. Cl.$^6$ .................................................. A61N 1/04
[52] U.S. Cl. ......................... 607/129; 128/642; 607/152
[58] Field of Search ........................... 607/120, 121, 607/119, 124, 132, 126, 129, 130, 131, 140, 148, 149, 152; 128/639, 640, 642; 606/32, 41

[56] References Cited

U.S. PATENT DOCUMENTS

| 2,893,105 | 7/1959 | Lauterbach | 128/DIG. 14 |
|---|---|---|---|
| 4,082,086 | 4/1978 | Page et al. | 128/640 |
| 4,144,889 | 3/1979 | Tyers et al. | 128/418 |
| 4,243,051 | 1/1981 | Wittemann | 607/152 |
| 4,291,707 | 9/1981 | Heilman et al. | 128/784 |
| 4,323,081 | 4/1982 | Wiebusch | 128/785 |
| 4,351,345 | 9/1982 | Carney | 128/786 |
| 4,444,207 | 4/1984 | Robicsek | 128/785 |
| 4,530,368 | 7/1985 | Saulson et al. | 128/784 |
| 4,541,440 | 9/1985 | Parsonnet | 128/785 |
| 4,693,258 | 9/1987 | Osypka et al. | 128/783 |
| 4,765,341 | 8/1988 | Mower et al. | 128/785 |
| 4,972,846 | 11/1990 | Owens et al. | 128/784 |
| 5,263,977 | 11/1993 | Adams et al. | 607/122 |
| 5,269,810 | 12/1993 | Hull et al. | 607/129 |
| 5,341,806 | 8/1994 | Gadsby et al. | 128/640 |

FOREIGN PATENT DOCUMENTS

| 0095727 | 12/1983 | European Pat. Off. | A61N 1/04 |

OTHER PUBLICATIONS

Medtronic Model 6500 Temporary Myocardial Pacing Lead Brochure (MC 873026).

Ausubel, et al., "Maintenance of Exercise Stroke Volume During Ventricular Versus Atrial Synchronous Pacing: Role of Contractility", CIRCULATION, vol. 72, No. 5, Nov. 1985 pp. 1037–1043.

Baller, et al., "Basic Physiological Studies on Cardiac Pacing with Special Reference to the Optimal Mode and Rate after Cardiac Surgery", Thorac. Cardiovasc. Surgeon 29 (1981) 168–173.

Casavant, David A., "Parameters for Reliable Atrial Sensing With an External Temporary DDD Pacemaker Following Open Heart Surgery", Technical Concept Paper, Sep. 1993, Medtronic, Inc. Jul. 1993.

(List continued on next page.)

Primary Examiner—Angela D. Sykes
Assistant Examiner—Eric F. Winakur
Attorney, Agent, or Firm—Michael J. Jaro; Harold R. Patton

[57] ABSTRACT

A temporary atrial defibrillation lead featuring a polytetraflouroethylene ("TEFLON") felt pad in which three parallel stainless steel defibrillation wire electrodes are mounted. The pad contains holes which expose the electrode wires in a discontinuous fashion. The three electrode wires are merged into one polyurethane insulated lead body, proximal to the pad. At the proximal end of the lead body a stainless steel connector pin with break away needle are mounted, for percutaneous exteriorization of the lead pin, in an area separated from the surgical incision. The break away needle can be broken off to make the connector pin suitable to patient cable connection. The (polytetraflouroethylene ("TEFLON") pad is permanently implanted on the atria and remains implanted after removal of the temporary electrode sections. The temporary electrode sections may be removed by gently pulling them at their proximal end.

34 Claims, 3 Drawing Sheets

OTHER PUBLICATIONS

Del Nido, et al., "Temporary Epicardial Pacing after Open Heart Surgery: Complications and Prevention", Journal Of Cardiac Surgery, 4:99–103, Mar. 1989.

Keane et al., "Biphasic Versus Monophasic Waveform in Epicardial Atrial Defibrillation", NASPE Abstracts, PACE, vol. 15, Apr. 1992, Part II, p. 570.

Kirklin, J. W. "Medtronic Model 6500 Temporary Myocardial Lead", Barrat–Boyles BC (eds) Cardiac Surgery, New York, 1993. P210.

Leitch, et al., "The importance of age as a predictor of atrial fibrillation and flutter after coronary artery bypass grafting", J Thorac Cardiovasc Surg 1990;100:338–42.

McMullen et al., "Atrial activity during cardioplegia and postoperative arrhythmias", J Thorac Cardiovasc Surg 1987;94:558–65.

"Pacing with Atrial Wire Electrodes Management Following Open–Heart Surgery", Medtronic News/Dec. 1980, pp. 3–7.

Waldo, et al., "Use of Temporarily Placed Epicardial Atrial Wire Electrodes for the Diagnosis and Treatment of Cardiac Arrhythmias Following Open–Heart Surgery" J Thorac Carciovasc Surg 1978;76:500–5.

Waldo, et al., "Continuous Rapid Atrial Pacing to Control Recurrent of Sustained Supraventricular Tachycardias Following Open Heart Surgery", Circulation 54: 245–50, 1976.

Mann, et al., "Emergency Defibrillation Using a Temporary Pacing Electrode Catheter," Pace, vol. 8, Sep.–Oct., 1985, pp. 753–756.

Waldo, et al., "Use of Atrial Epicardial Wire Electrodes in the Diagnosis and Treatment of Arrhythmias Following Open Heart Surgery", Advances In The Management Of Arrythmias, D. T. Kelly, ED. Lane Cove, Australia: Telectronics Pty., 1978 pp. 287–306.

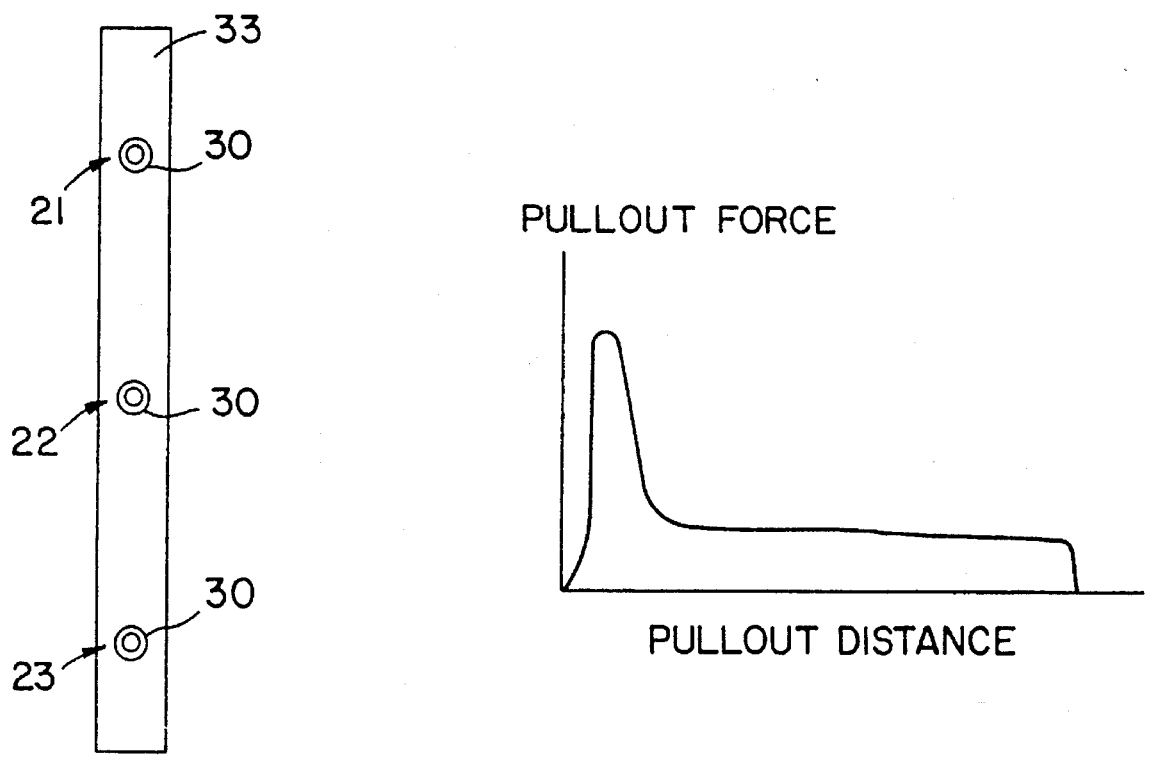
FIG. 7
FIG. 9
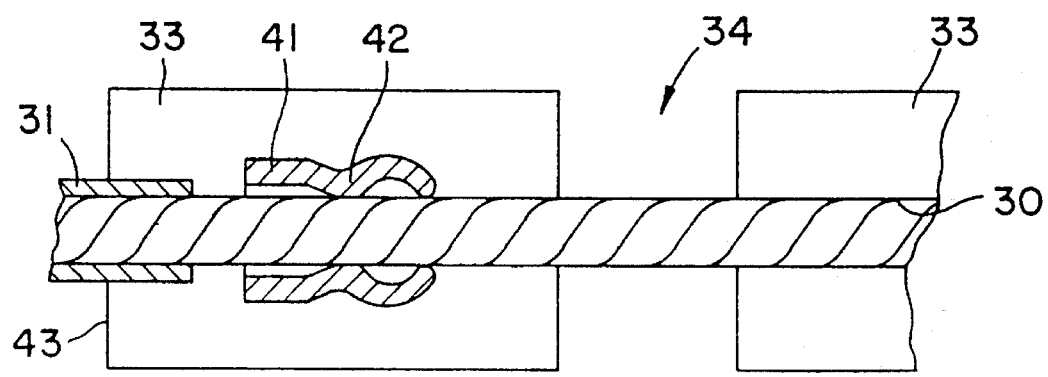
FIG. 8

TEMPORARY MEDICAL ELECTRICAL LEAD

FIELD OF THE INVENTION

The present invention relates to the field of cardiac stimulation and specifically to the field of temporary stimulation of cardiac tissue through a medical electrical lead.

BACKGROUND OF THE INVENTION

Atrial arrhythmias and supra ventricular tachycardias, such as atrial fibrillation, atrial flutter and atrio-ventricular reentries, are a common postoperative complication among patients who have had heart surgery. See, for example, Cardiac Surg. Kirklin J. W., Barrat-Boyes B. C. (Eds.): NY 1993, pg. 210. During the first 10 days after heart surgery it is estimated postoperative supra ventricular tachycardia occurs in up to 63 percent of patients. See, for example, "The Importance of Age as a Predicator of Atrial Fibrillation and Flutter After Coronary Artery Bypass Grafting" Leitch et al., J. Thorac. Cardiovasc. Surg., 1990:100:338–42; "Atrial Activity During Cardioplegia and Postoperative Arrhythmias", Mullen et al., J. Thorac. Cardiovasc. Surg., 1987:94:558–65.

The presence of these arrhythmias, which in an otherwise healthy patient may not be unduly serious, may be especially harmful to heart surgery patients. The hemodynamic condition of these patients is often already compromised by either the surgery itself or the effects of prolonged anaesthesia or both. Supra ventricular tachycardias may further cause a very irregular ventricular rate which may even further deteriorate their hemodynamic condition. Such further deterioration is especially serious for patients with a compromised left ventricular function. These complications may present a serious impediment to the recovery of the patient. See, for example, "Maintenance of Exercise Stroke Volume During Ventricular Versus Atrial Synchronous Pacing: Role of Contractility" Ausubel et al., Circ., 1985:72(5):1037–43; "Basic Physiological Studies on Cardiac Pacing with Special Reference to the Optimal Mode and Rate After Cardiac Surgery" Baller et al., Thorac. Cardiovasc. Surg., 1981:29:168–73.

Due to the serious and potentially life threatening nature of these conditions, postoperative treatment is often aimed at preventing arrhythmias, such as through drugs. Drugs, however, have been found to not always be effective at preventing arrhythmias. Thus it is often necessary to provide a means for terminating any arrythymias which may occur. One common method used has been through over-pacing.

For example Waldo et al. in "Use of Temporarily Placed Epicardial Atrial Wire Electrodes For The Diagnosis and Treatment of Cardiac Arrhythmias Following Open-Heart Surgery, . "J. Thorac. Cardiovasc. Surg., 1978, vol 76, no. 4, pgs. 558–65 discloses the use of a pair of temporary heart wires placed on the atrium to diagnose and treat arrhythmias by antitachy overdrive pacing. Specifically the temporary heart wires were sutured to the atrial wall at the time of the heart surgery. Once the patient was ready to be released the wires were removed by traction or pulling upon their external end.

Temporary postoperative atrial and ventricular pacing with temporary heart wires has been found to successfully treat many of the potential post-operative arrhythmias. As such the procedure has become widespread—at least 100,000 procedures per year. Several problems, however, were encountered with the system disclosed by Waldo et al., referred to above. One problem was the stability of the heart wire within the atrial wall. Because the wall undergoes constant motion, the temporary heart wire lead was found to dislodge an unacceptable amount. Secondly, the relatively thin atrial wall, especially on elderly patients, was sometimes torn by traction upon the lead for removal.

An improved method of temporarily affixing heart wires onto the atrium was achieved with the introduction of the Medtronic Model 6500 Temporary Myocardial Pacing Lead System. That lead system featured a silicone atrial fixation disk to fasten the lead to the atrium. Specifically the silicone atrial fixation disk was permanently sutured to the atrium. The lead was positioned so that it was trapped between the disk and the atrial tissue. The lead could thereby be removed by simply pulling it from between the disk and the tissue. The rubber disk remained in the body after removal of the electrodes. The advantages offered by such a fixation system included more reliable lead fixation along with protecting the relatively thin atrial walls from tearing during lead removal. Thus the Medtronic Model 6500 Temporary Myocardial Pacing Lead permitted post-surgical temporary antitachy over-drive pacing to be performed more safely.

In spite of the improved systems or methods to achieve antitachy overdrive pacing it is not, however, always effective in terminating postoperative atrial arrhythmias or supra ventricular tachycardias. When drugs and over-pacing are not effective in the prevention or termination of postoperative supra ventricular tachycardias, or because of main negative inotropic side effects relatively contraindicated, it may become necessary to perform atrial defibrillation, synchronized to the R-wave of the electrogram, to terminate these potentially life-threatening arrythmia. Because of the large energies involved for defibrillation, however, the temporary heart wires could not be used.

External atrial defibrillation, although an effective treatment, has profound side effects. First it should be noted that in contrast to ventricular defibrillation, where conversion to normal sinus rhythm is required at the first shock, atrial defibrillation may be obtained after several shocks because ventricular contraction continues during supra ventricular tachycardia. In addition, due to the high energy required (40 to 360 Joules), the application of shocks, besides their number, is not tolerated well by a conscious patient. Therefore external defibrillation is preferably performed under general anaesthesia or at least sedation. Of course the use of anesthesia gives rise to another risk to the patient.

External defibrillation requires relatively high energy because the electrical source is not positioned directly upon the cardiac tissue but rather must pass through the thorax, which tends to dissipate the energy. In contrast, internally applied atrial defibrillation, such as may occur during surgery through defibrillation paddles placed directly on the heart, requires considerably less energy because the defibrillation electrical energy is applied only to the tissue that needs to be defibrillated. In fact, direct atrial defibrillation may be accomplished with only 1.0 Joule pulses in contrast to the 40 Joule and greater pulses for external defibrillation. See, for example, Kean D., NASPE abs. 246, PACE, April 1992, pt. II, pg. 570.

It should be understood the defibrillation success rate is dependent on the delivered energy. The lower the energy, the lower the success rate and the higher the number of shocks to be applied to obtain defibrillation success. With direct atrial defibrillation, because the energy may be applied directly to the heart, the energy level can be chosen such that both the shock level as well as the number of shocks required may be tolerated by the patient.

SUMMARY OF THE INVENTION

It is thus an object of the present invention to provide a temporary atrial defibrillation lead which is capable of providing electrical stimulation pulses of sufficient energy to result in defibrillation at a tolerable level.

It is a further object of the invention to provide a temporary atrial defibrillation lead which may provide sufficient energy to the atrium so as to be tolerated by the patient and therefore delivered without the necessity of general anaesthesia.

It is a further object of the invention to provide a temporary atrial defibrillation lead which may be reliably fixed to the atrium through a fixation pad.

It is a further object of the invention to provide a temporary atrial defibrillation lead which may be safely and reliably removed from the atrium.

It is a further object of the invention to provide a temporary atrial defibrillation lead which may be safely and reliably removed from the atrium without the necessity of a surgical intervention.

In accordance with the above objects there is provided a temporary atrial defibrillation lead featuring a polytetraflouroethylene ("TEFLON") felt pad in which three parallel stainless steel defibrillation wire electrodes are mounted. The pad contains holes which expose the electrode wires in a discontinuous fashion. The three electrode wires are merged into one polyurethane insulated lead body, proximal to the pad. At the proximal end of the lead body a stainless steel connector pin with break away needle are mounted for the percutaneous exteriorization of the lead pin in an area separated from the surgical incision. The break away needle can be broken off to make the connector pin suitable for connection to a therapeutic device, such as a defibrillator. The polytetraflouroethylene ("TEFLON") pad is permanently implanted on the atria and remains implanted after removal of the temporary electrode sections. The temporary electrode sections may be removed by gently pulling them at their proximal end.

BRIEF DESCRIPTION OF THE DRAWINGS

Other objects, advantages and features of the present invention will become apparent from the following specification when taken in conjunction with the accompanying drawings in which like elements are commonly enumerated and in which:

FIG. 7 is a sectional view of the lead shown in FIG. 6 taken along line 7—7.

FIG. 8 is a sectional detail of the stranded conductor and bus within the mounting pad.

FIG. 9 is a graph illustrating the force required to remove a lead according to the present invention.

The drawings are not necessarily to scale.

DETAILED DESCRIPTION OF THE PREFERRED EMBODIMENT

Figure 1:
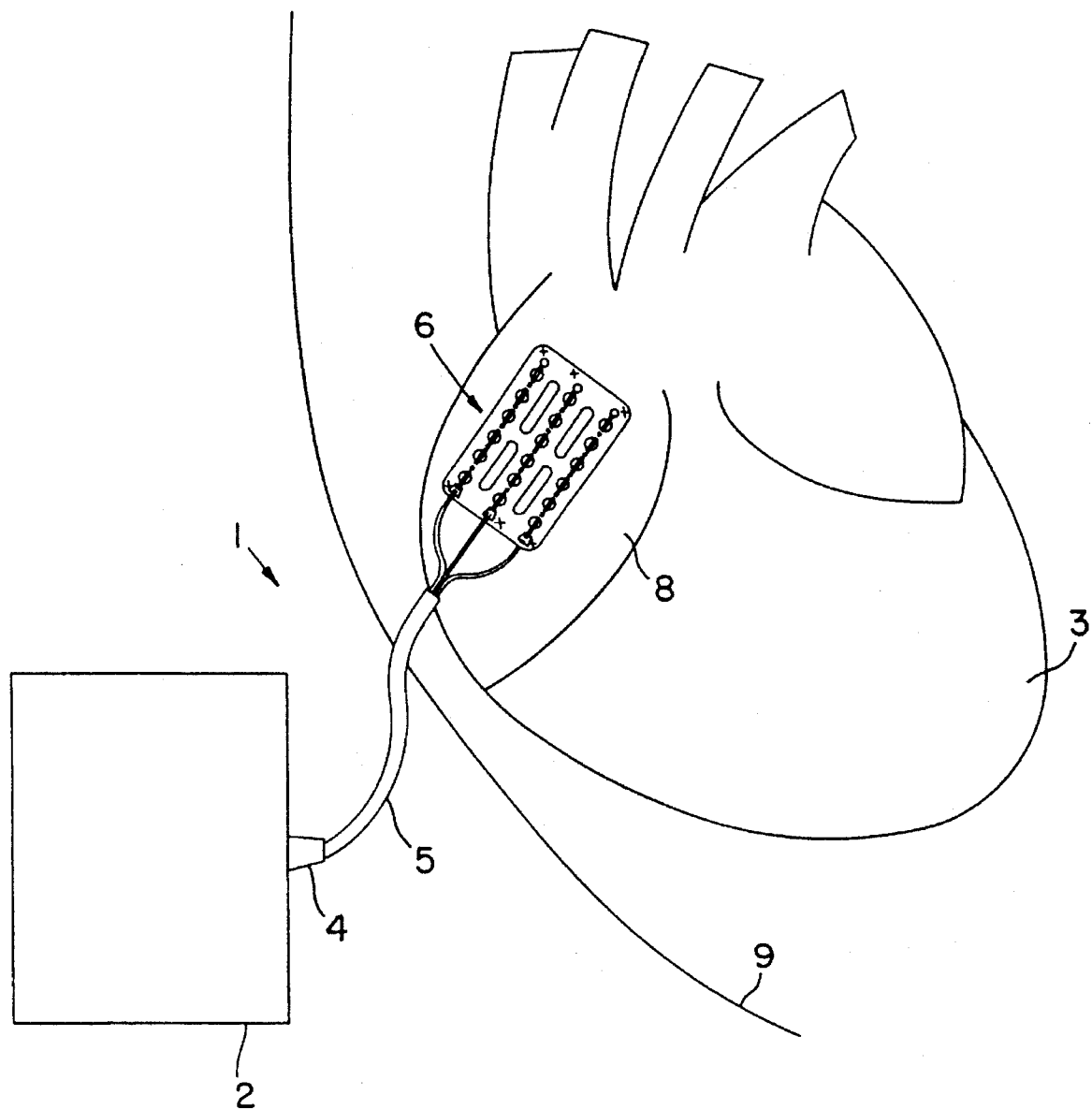
FIG. 1 is a plan view of a lead according to the present invention used to connect a pulse generator to a heart.

FIG. 1 is a plan view of a lead 1 according to the present invention used to connect pulse generator 2 to heart 3. As seen lead 1 has essentially three sections: connector assembly 4, lead body 5 and electrode assembly 6.

Figure 2:
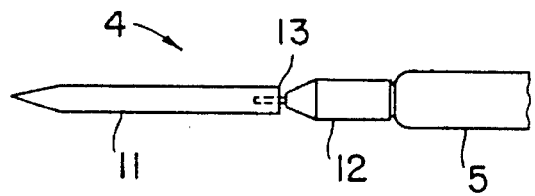
FIG. 2 details the connector assembly used in a lead according to the present invention having the break-away needle attached.
Figure 3:
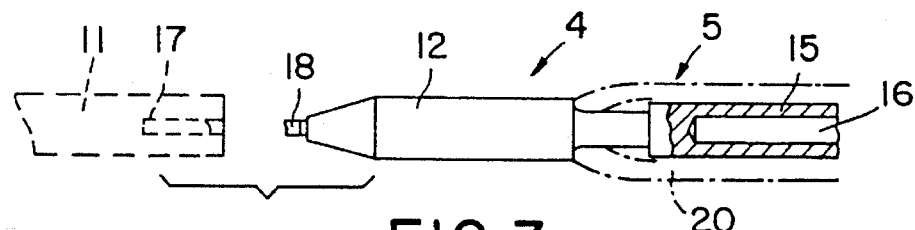
FIG. 3 details the connector assembly used in a lead according to the present invention having the break-away needle broken away.

Connector assembly 4 connects lead 1 to pulse generator 2. Details of connector assembly 4 may be seen in FIGS. 2 and 3. As seen connector assembly 4 features a break-away needle 11 which mates with pin assembly 12. Specifically break-away needle 11 has recess 17 which mates with finger 18 of pin assembly 12. In the preferred embodiment pin assembly 12 is stainless steel. Break-away needle 11 is provided on pin assembly 12 to permit the passage of connector assembly 4 from inside the body, through the skin to outside the body. Break-away needle 11 may thereafter be broken off connector assembly 4 at breakpoint 13 to thereby permit pin assembly 12 to join to a pulse generator 2. As seen in FIG. 3 when break-away needle 11 is broken off it carries with it a portion of finger 18. Pin assembly 12 further features crimp skirt 15 to permit conductors of lead body 5 to be joined thereto. Specifically conductors are crimped within cavity 16 and thereby electrically connected to pin assembly 4.

Figure 4:
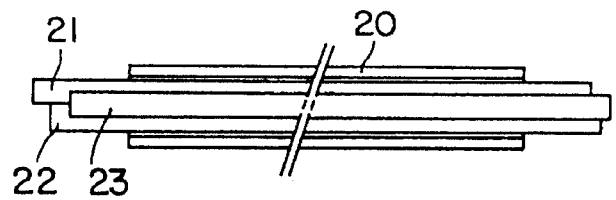
FIGS. 4 and 5 detail the lead body used in a lead according to the present invention.
Figure 5:
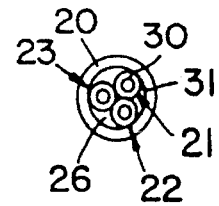

Lead body 5 consists of an insulative outer sleeve 20 encasing a plurality of conductors 21, 22 and 23 as seen in FIGS. 4 and 5. Gap 26 among inner conductors 21, 22 and 23 is filled by medical adhesive. Outer sleeve 20 may be constructed from any suitable biocompatible material, however in the preferred embodiment outer sleeve 20 is polyurethane.

Inner conductors 21, 22, and 23 are each constructed in a similar fashion and thus only one need be described. Inner conductor 21 is constructed from a stranded conductor 30 encased by inner sleeve 31. In the preferred embodiment stranded conductor 30 is a multi-filament stainless steel stranded wire and inner sleeve 31 is polyurethane. It should be understood, of course, that any suitable material or wire could be used for conductor 30 including a coiled wire as well as any type of wire made from an acceptable biocompatible metal including, but not limited to, such materials as platinum, palladium, titanium, tantalum, rhodium, iridium, carbon, vitreous carbon and alloys, oxides and nitrides of such metals or other conductive materials. Of course, some materials are incompatible with others and may not be effectively used together. The limitations of specific materials for use with others is well known in the art. It should also be understood that any other suitable material could also be used for inner sleeve 31 such as silicone, for example.

Figure 6:
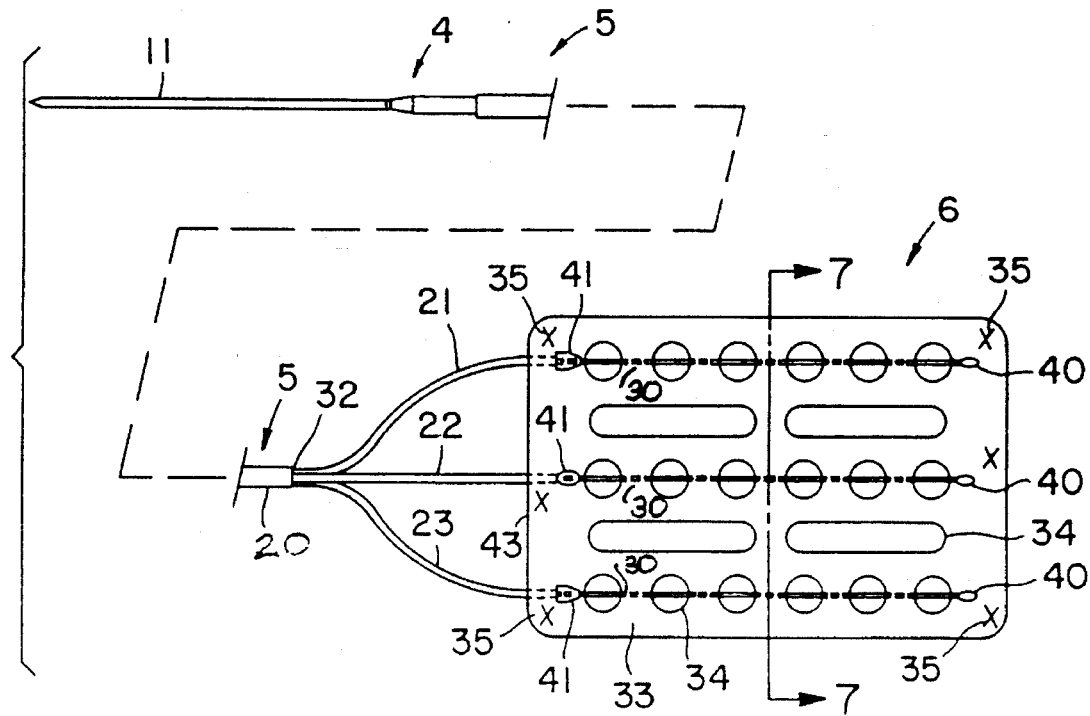
FIG. 6 is a plan view of a lead according to the present invention.

As best seen in FIG. 6 outer sleeve 20 ends at a point 32 away from the distal end of lead 1. Inner conductors 21, 22, and 23 extend from point 32 to electrode assembly 6. Electrode assembly 6 is formed with inner conductors 21, 22, 23 and mounting pad 33. Specifically distal portion of each inner conductor has stranded conductor 30 exposed along the length of mounting pad 33. Each of the inner conductors 30 is mounted to mounting pad 33, as best seen in FIGS. 7 and 8. Although the illustrated preferred embodiment features inner conductors 30 mounted within mounting pad 33, it should be understood inner conductors may be mounted to mounting pad 33 in any acceptable manner including, without limiting the variations possible, suturing or gluing all or some of inner conductor 30 to an outer surface of the mounting pad 33. In the preferred embodiment holes 34 within mounting pad 33 are used to provide for intermittent sections of each stranded conductor 30 to be exposed to body tissue. Thus when lead 1, and specifically electrode assembly 6, is mounted to cardiac tissue, intermittent sections of each stranded conductor 30 are directly exposed to cardiac tissue through holes 34. Mounting pad 33 further features suture areas 35 (designated by "x"s in the FIGS.) which permit mounting pad 33 to be sutured to the heart, as best seen in FIG. 1. Mounting pad 33 may be fashioned from any biocompatible pliant, material and in the preferred embodiment mounting pad 33 is fashioned from a polytetraflouroethylene ("TEFLON") felt.

Implantation of lead 1 according to the present invention is as follows. Mounting pad 33 is sutured to atrium 8 using suture areas 35. Next connector assembly 4 is exteriorized at a point away from the incision through use of break-away needle 11 and pin assembly 12. Specifically needle 11 is used to pierce the skin from the interior to the exterior so as to expose pin assembly 12. Once lead 1 is satisfactorily sutured to the atrium, pin assembly 12 exposed and the lead connected to a pulse generator, the patient's incision may be closed. At this point lead 1 may deliver therapeutic electrical pulses, including defibrillating, cardioverting or pacing, to atrium 8.

One important aspect of the lead of the present invention is its removability. Inner conductors 21, 22, 23 are mounted within mounting pad 33 so they may be removed, even once implanted, by traction. Specifically the inner conductors may be gently removed from mounting pad 33, and thus body 9, by traction upon proximal end of lead 1.

As seen in FIGS. 7 and 8 inner conductors are positioned within mounting pad 33. Bus 41 is crimped to the conductor. Bus 41 serves to prevent unintended dislodgement of inner conductor 30 out of mounting pad 33. Bus 41 is placed at the proximal end 43 of pad 33, at a point between end 43 of pad 33 and hole 34. As such when inner conductor 30 is removed by traction, bus 41 only needs to pass through a short portion of pad 33 before it is free. Thus only a relatively brief amount of increased force, i.e. a short "jerk" or tug on the distal end of lead body 5 is sufficient to pull bus 41 out of pad 33. Once bus 41 is outside pad 33 the remainder of inner conductor 30 follows easily as there is no other structure along the length of inner conductor 30 which will inhibit the travel of inner conductor 30 through pad 33. This is illustrated in FIG. 9 where it is illustrated that pullout distance initially requires a relatively great pullout force, but which rapidly decreases once bus 41 is withdrawn from mounting pad 33. Thus it may be seen that bus 41 prevents inner conductors 21, 22, 23 from accidentally dislodging from position while also allowing their intended dislodgement and removal without possibly excessive forces from being applied to the atrium 8 during removal. In the preferred embodiment a small amount of medical adhesive 40 is applied to the distal end of each conductor 30 in order to cap off the ends of the stranded wire. This is done in order to keep the strands together and to prevent damage to the tissue during the removal procedure or in case the conductor would be forced out of the pad while implanted, as could occur due to heart movement. Mounting pad 33 because it is sutured to the heart, is left in place once conductors and lead body are removed.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A temporary medical electrical lead comprising:

a mounting pad of a pliant biocompatible material, said pad having a series of holes;

a plurality of elongate members, each said member comprising a conductor having a distal region and a proximal region and an insulative sleeve covering said proximal region of said conductor, said distal region of said conductor mounted within said pad in a position in which at least one of said elongate members intersects at least one of said holes, said distal region of said conductor having means for temporarily affixing the conductor to the pad, said distal region of said conductor communicating with an exterior of said pad in the region of each of said holes.

2. A temporary medical electrical lead according to claim 1 further comprising said means for temporarily affixing the conductor to the pad fastened to said conductor at a point within said distal region.

3. A temporary medical electrical lead according to claim 1 further comprising said plurality of elongate members mounted within said pad in parallel.

4. A temporary medical electrical lead according to claim 1 wherein said pad is porous.

5. A temporary medical electrical lead according to claim 1 wherein said pad is polytetraflouroethylene felt.

6. A temporary medical electrical lead according to claim 1 wherein said conductor is a stranded wire.

7. A temporary medical electrical lead according to claim 1 further comprising a proximal end of said conductor attached to a connector pin assembly.

8. A temporary medical electrical lead according to claim 7 further comprising a needle attached to said connector pin assembly.

9. A temporary medical electrical lead comprising:

a mounting pad of a pliant biocompatible material;

a plurality of elongate members, each said member comprising a conductor and an insulative sleeve, said conductor having a distal region and a proximal region, said insulative sleeve covering said proximal region of said conductor, said distal region of said conductor mounted within said pad, said distal region of said conductor having means for temporarily affixing the conductor to the pad, said distal region of said conductor communicating with an exterior of said pad.

10. A temporary medical electrical lead according to claim 9 wherein said pad has a series of holes, said elongate members are mounted within said pad in a position in which they intersect at least one of said holes.

11. A temporary medical electrical lead according to claim 9 wherein said means for temporarily affixing the conductor to the pad is fastened to said conductor at a point within said distal region.

12. A temporary medical electrical lead according to claim 9 wherein said plurality of conductors are mounted in parallel.

13. A temporary medical electrical lead according to claim 9 wherein said pad is polytetraflouroethylene felt.

14. A temporary medical electrical lead according to claim 9 wherein said conductor is a stranded wire.

15. A temporary medical electrical lead according to claim 9 further comprising a proximal end of said conductor attached to a connector pin assembly.

16. A temporary medical electrical lead according to claim 15 further comprising a needle attached to said connector pin assembly.

17. A temporary medical electrical lead comprising:

a mounting pad of a pliant biocompatible material, said pad having a series of holes at least one elongate member comprising a conductor and an insulative sleeve, said conductor having a distal region, a distal end, and a proximal region, said insulative sleeve covering said proximal region of said conductor, said distal region of said conductor mounted within said pad, said distal region of said conductor having means for temporarily affixing the conductor to the pad, said distal region of said conductor communicating with an exterior of said pad, said at least one elongate member is mounted within said pad in a position in which said at least one elongate member intersects across at least one of said holes distal end of said conductor is mounted within said pad.

18. A temporary medical electrical lead according to claim 17 wherein said pad is polytetraflouroethylene felt.

19. A temporary medical electrical lead according to claim 17 wherein said conductor is a stranded wire.

20. A temporary medical electrical lead according to claim 17 further comprising a proximal end of said conductor attached to a connector pin assembly.

21. A temporary medical electrical lead according to claim 20 further comprising a needle attached to said connector pin assembly.

22. A temporary medical electrical lead comprising:

a mounting pad of a pliant biocompatible material, said pad having a first surface and a second surface;

a plurality of elongate members attached to said mounting pad, each said member comprising a conductor and an insulative sleeve, said conductor having a distal region and a proximal region, said insulative sleeve covering said proximal region of said conductor, said distal region of said conductor having means for temporarily affixing the conductor to the pad, said distal region of said conductor connected to said pad by said means for temporarily affixing the conductor to the pad.

23. A temporary medical electrical lead according to claim 22 wherein said plurality of conductors are attached in parallel.

24. A temporary medical electrical lead according to claim 22 wherein said conductor is a stranded wire.

25. A temporary medical electrical lead according to claim 22 further comprising a proximal end of said conductor attached to a connector pin assembly.

26. A temporary medical electrical lead according to claim 25 further comprising a needle attached to said connector pin assembly.

27. A temporary medical electrical lead according to claim 22 wherein said plurality of conductors are attached within said pad.

28. A temporary medical electrical lead according to claim 22 wherein said plurality of conductors are attached to a first surface of said mounting pad.

29. A temporary medical electrical lead comprising:

a mounting pad of polytetraflouroethylene felt, said pad having a first surface and a second surface;

a plurality of elongate members attached to said mounting pad, each said member comprising a conductor and an insulative sleeve, said conductor having a distal region and a proximal region, said insulative sleeve covering said proximal region of said conductor, said distal region of said conductor mechanically connected to said pad, each said plurality of conductors are attached in parallel to said pad, each said conductor having means for temporarily affixing the conductor to the pad.

30. A temporary medical electrical lead according to claim 29 wherein said conductor is a stranded wire.

31. A temporary medical electrical lead according to claim 29 further comprising a proximal end of said conductor attached to a connector pin assembly.

32. A temporary medical electrical lead according to claim 31 further comprising a needle attached to said connector pin assembly.

33. A temporary medical electrical lead according to claim 29 wherein said plurality of conductors are attached within said pad.

34. A temporary medical electrical lead according to claim 29 wherein said plurality of conductors are attached to a first surface of said mounting pad.

* * * * *